Figure 1:
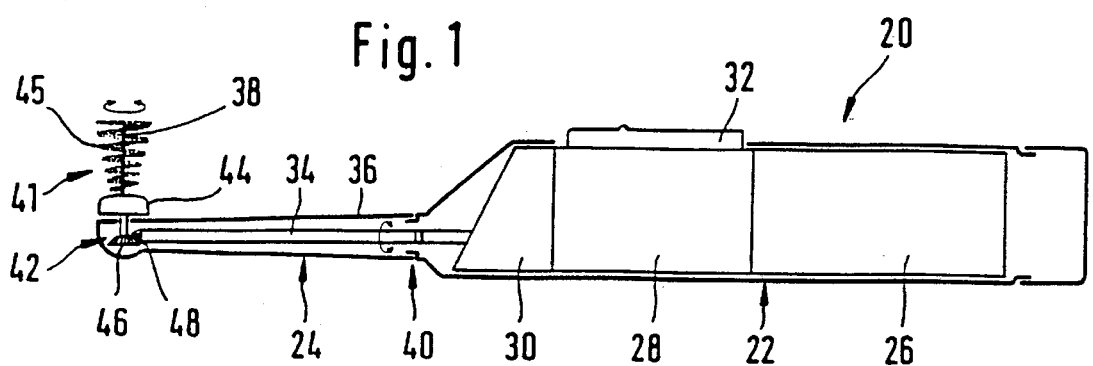

United States Patent [19]
Hilfinger et al.

[11] Patent Number: 5,613,258
[45] Date of Patent: Mar. 25, 1997

[54] TOOTHBRUSH

[75] Inventors: Peter Hilfinger, Bad Homburg; Bernhard Boland, Frankfurt am Main, both of Germany

[73] Assignee: Braun Aktiengesellschaft, Kronberg, Germany

[21] Appl. No.: 614,191

[22] Filed: Mar. 12, 1996

Related U.S. Application Data

[63] Continuation of Ser. No. 385,235, Feb. 8, 1995, abandoned, which is a continuation of Ser. No. 50,366, filed as PCT/EP92/01773, Aug. 5, 1992, abandoned.

[30] Foreign Application Priority Data

Sep. 16, 1991 [DE] Germany ............ 41 30 741.0
Nov. 5, 1991 [DE] Germany ............ 41 36 376.0
Aug. 5, 1992 [WO] WIPO .......... PCT/EP92/01773

[51] Int. Cl.⁶ .................................. A46B 13/02
[52] U.S. Cl. .................. 15/22.1; 15/23; 15/206; 433/118
[58] Field of Search .................. 15/22.1, 22.2, 15/23, 24, 26, 206, 167.1, 79; 433/118, 125

[56] References Cited

U.S. PATENT DOCUMENTS

| | | | |
|---|---|---|---|
| 880,277 | 2/1908 | Chandler | 15/26 |
| 1,172,792 | 2/1916 | Hamel | 15/26 |
| 1,481,891 | 1/1924 | Cruikshank | 15/26 |
| 1,593,763 | 7/1926 | Henderson | 15/23 |
| 1,854,626 | 4/1932 | Riggall, Jr. | 15/23 |
| 1,860,894 | 5/1932 | Lieux | 15/23 |
| 2,172,024 | 9/1939 | Haluss | 15/23 |
| 2,435,421 | 2/1948 | Blair | 15/23 |
| 2,624,062 | 1/1953 | Knoderer . | |
| 2,840,837 | 1/1958 | Gustens | 15/23 |
| 2,841,806 | 7/1958 | Blasi | 15/24 |
| 3,204,275 | 9/1965 | Baker . | |
| 3,925,841 | 12/1975 | Caliendo | 15/23 |
| 3,939,520 | 2/1976 | Axelsson . | |
| 4,387,479 | 6/1983 | Kigyos . | |
| 4,751,761 | 6/1988 | Breitschmid . | |
| 4,880,382 | 11/1989 | Moret et al. | 433/118 |
| 5,000,684 | 3/1991 | Odrich | 433/118 |
| 5,071,348 | 12/1991 | Woog | 433/118 |

FOREIGN PATENT DOCUMENTS

| | | | |
|---|---|---|---|
| 987083 | 8/1951 | France | 15/26 |
| 2515013 | 4/1983 | France | 15/23 |
| 2926994 | 7/1979 | Germany . | |
| 3011534 | 10/1981 | Germany | 15/23 |
| 9014271 U | 10/1990 | Germany . | |
| 3937850 | 5/1991 | Germany . | |
| 3937853 | 5/1991 | Germany . | |
| 258378 | 4/1928 | Italy | 15/26 |
| 240682 | 12/1946 | Switzerland | 15/23 |
| 292744 | 11/1953 | Switzerland | 15/26 |

Primary Examiner—Tony G. Soohoo
Attorney, Agent, or Firm—Fish & Richardson, P.C.

[57] ABSTRACT

The invention is directed to a brush for cleaning the teeth, the brush being suitable for use in a toothbrush having a handle member and a brush member and comprising a bristle supporting structure and bristles fixedly secured thereto. The bristle supporting structure is configured as a rod-shaped stem having a first and a second end portion and carrying no bristles in the region of the second end portion. The bristles extend radially relative to the stem in the region of the first end portion and are arranged in a circumferentially distributed pattern. The length of the bristles decreases starting from the first end portion of the stem in the direction of the second end portion of the stem. This brush allows effective and gentle cleaning of the teeth, in particular the interproximal spaces thereof.

21 Claims, 3 Drawing Sheets

TOOTHBRUSH

This is a continuation of application Ser. No. 08/385,235, filed Feb. 8, 1995, now abandoned, which is a continuation of application Ser. No. 08/050,366, filed as PCT/EP92/01773, Aug. 5, 1992, now abandoned.

This invention relates to a brush for cleaning the teeth, in particular the interproximal area, the brush being suitable for use in a toothbrush having a handle member and a brush member. The brush is comprised of a bristle supporting structure and bristles fixedly secured thereto, the bristle supporting structure being configured as a rod-shaped stem having a first and a second end portion and carrying no bristles in the region of the second end portion. The bristles extend radially relative to the stem in the region of the first end portion and are arranged in a circumferentially distributed pattern.

From printed specification DE 90 14 271 U1, a toothbrush of this type is already known. The electrically powered toothbrush disclosed therein includes a driving mechanism for the brush causing the brush to perform rotary motions. As this occurs, the brush rotates about an axis disposed normal to the longitudinal axis of the brush handle member. The brush itself is of a cylindrical or, alternatively, conical configuration, with the tip of the cone being arranged at the first end portion. This electric toothbrush claims to be especially suited to the cleaning of teeth in cases where fixed braces are used. However, when this electric toothbrush is used for cleaning in particular the area interproximately of the teeth, danger exists that the bristle supporting structure configured as a rod-shaped stem contacts the teeth or the gums during the cleaning operation, causing damage to the tooth surface or injuring the gums.

Further, from U.S. Pat. No. 4,751,761 or U.S. Pat. No. 4,387,479, hand-operated toothbrushes for cleaning in particular the interproximal area are known, in which the bristle support configured as a rod-shaped stem is comprised of a twisted two-wire arrangement, and the bristles are fixedly secured between the wires of the two-wire arrangement. These brushes for hand-operated toothbrushes are equally of a cylindrical or conical configuration, with the tip of the cone being associated with the first end portion of the stem. Also when these brushes in which the bristle support is composed of metal wire are used in practice, the risk exists that the tip at the first portion of the bristle support causes gum injury or damage to the tooth surface. In addition, these hand-operated interproximal brushes are not particularly well suited to the cleaning of small interproximal spaces. The reason for this is that the user, in accordance with the recommendations of the manufacturers of such known interproximal brushes, is required to introduce the stem of the brush into the interproximal space for cleaning it, using a to-and-fro motion. Considering that the stem diameter is in the range of between 0.2 mm and 0.4 mm, the interproximal brush cannot be introduced into tight interproximal spaces. Moreover, also the bristles of such brushes are hardly in a position to enter the interproximal areas, because the first end portion which is best suitable for cleaning in respect of manipulation practically carries no bristles at all or only very short bristles (conical brush). Where brushes of a cylindrical configuration are used, the bristles are equally capable of entering the interproximal spaces to a very small extent only, because adjacent bristles bear against the tooth outer or inner surfaces.

It is an object of the present invention to devise a brush for a toothbrush which produces especially good cleaning results, in particular when cleaning interproximal areas, avoiding to the largest possible extent gum injuries or damage to the tooth surfaces by the bristle supporting structure.

This object is essentially accomplished in that in a brush incorporating the features initially identified the length of the bristles is larger in the region of the first end portion of the stem than in a region in the center of the bristled portion of the stem.

A brush embodying these features results in the following advantages:

When the bristle supporting structure of the brush is guided parallel to the outer or inner surfaces of the teeth—unlike the conventional, recommended cleaning movement, the longer bristles provided on the first end portion are capable of entering the interproximal spaces between the teeth extremely effectively, producing an efficient cleaning action in these areas. Also the tooth-gingiva junction region is well covered and efficiently cleaned by the longer bristles on the first end portion. Maneuvering the brush in this manner eliminates the danger of the bristle supporting structure contacting the teeth or the gums, because the shorter bristles are engaged against the teeth, while the longer bristles penetrate the interproximal spaces. By contrast, when the bristle supporting structure of the brush is introduced into an interproximal space between two adjacent teeth as is conventional practice, the longer bristles arranged on the first end portion and engaged against adjacent sides of the two teeth prevent any direct contact from occurring between the teeth or gums and the bristle supporting structure. Accordingly, also this manner of manipulating the brush practically eliminates the possibility of injury or damage.

In an embodiment of the present invention, the length of the bristles diminishes preferably linearly in the direction of the second end portion of the stem, starting from the first end portion of the stem. The brush assumes the shape of a circular cone or frustum of a cone, with the tip of the cone or the smaller diameter of the frustum pointing to the base of the bristle supporting structure, that is, in the direction of the second end portion of the bristle supporting structure. Owing to the large diameter of the brush in the area of the first end portion, gums and teeth are effectively protected against contact with the bristle supporting structure.

With a diameter diminishing from values in the range of 10±2 mm to values in the range of 5±2 mm, the brush is rather large as compared with conventional hand-operated and motor-powered interproximal brushes. Nevertheless, an excellent cleaning action is produced due to the modified shape and manipulation of the brush—guiding the bristle supporting structure parallel to the tooth outer or inner surfaces.

In a further feature of the present invention, the bristle thickness in the first end portion of the brush decreases from values in the range of 6±1 mils (1 mil corresponding to 0.0254 mm) to values in the range of 4±1 mils in the direction of the second end portion. The cleaning action of the brush is further improved by the use of bristles of greater hardness in the area of the first end portion.

In an advantageous embodiment, with the relative distance to the first end portion increasing, the length of the bristles diminishes in steps, in particular, in a single step. By this means, a brush is suggested which, starting from the first end portion, forms a cylinder of a large diameter, with a cylinder of a reduced diameter lying adjacent thereto. Starting from the first end portion, the step is preferably provided after about one third of the overall length of the bristled portion of the brush. This results in the advantage that in the use of the brush its reduced-diameter cylinder bears against a tooth inner or outer surface, while its larger-diameter cylinder enters the interproximal space for cleaning purposes.

An advantageous dimensioning of the brush is obtained in that the diameter of the larger cylinder assumes a value in the range of 12±2 mm, and the diameter of the smaller cylinder assumes a value in the range of 6±2 mm.

In an advantageous feature of the present invention, the bristle thickness in the first end portion of the brush is in the range of 6±1 mils, while the bristle thickness in the direction of the second end portion decreases to values in the range of 4±1 mils.

In a further embodiment of the present invention, starting from the first end portion of the stem, the length of the bristles diminishes initially in the direction of the center of the bristled portion of the stem, subsequently increasing again in the direction of the second end portion of the stem. The brush thus assumes the shape of two frustums of a cone having the surfaces of their smaller-diameter areas adjacent to each other. By virtue of the larger diameters at the respective ends of the bristled portion, teeth and gums are well protected against contact with the bristle supporting structure. The large diameter of the brush at the first end portion enables a very good cleaning action to be performed on the tooth sides in the interproximal space. Finally, the reduced diameter of the brush in the center area of the bristled portion substantially facilitates the typical interproximal cleaning movement involving a circular movement of the brush in the interproximal space, because the brush is automatically held in the center area due to the larger diameters at the respective ends of the bristled portion which serve a boundary function.

It is an advantage in this embodiment of the present invention when the length of the bristles initially decreases linearly with the axial distance from the first end portion of the stem increasing, subsequently increasing again linearly. Equally, it is advantageous when the smallest diameter of the brush is provided symmetrically in the center of the bristled portion of the stem.

An advantageous dimensioning of the brush is obtained by arranging for the diameter of the brush to decrease initially from a value in the range of 8±2 mm to a value in the range of 4±2 mm, subsequently increasing again to a value in the range of 8±2 mm.

A bristle thickness in the range of 6±1 mils has proven to be advantageous.

In accordance with a further feature of the present invention, the axial length of the first portion of the stem assumes values in the range of 12±3 mm, and the axial length of the second portion of the stem assumes values in the range of 9±3 mm. By this means, a sufficient length of the bristled portion of the stem is ensured in order to obtain a good cleaning effect, while the stem portion carrying no bristles is dimensioned sufficiently long to secure it to a brush holder by injection molding, insertion, or some other securing technique.

Further, it is advantageous when the stem is comprised of a twisted two-wire arrangement and the bristles are fixedly secured between the wires of the two-wire arrangement.

In a particularly advantageous feature of the present invention, a brush, in particular of the type described in the foregoing, is caused to perform an oscillating rotary motion about the stem axis by means of a motor drive mechanism, with the angle of oscillation preferably assuming values in the range of ±35° ±5°. By this means, the following inconvenient, under circumstances even hazardous, effect is avoided which occurs in toothbrushes in which the brush is driven to rotate in a single direction. When such toothbrushes are equipped with interproximal brushes whose stem is made of a twisted two-wire arrangement, the twisted stem may, so to speak, act as a thread which, with the brush rotating in the appropriate direction, threads itself into the space interproximately of two teeth up to the stop on the bristle supporting structure, without the user being in a position to prevent this from occurring. This then gives rise to the likelihood of major damage to the user's tooth surfaces or gums. A remedy is offered in the use of a brush adapted to perform an oscillating rotary motion about the stem axis. The angle of oscillation is preferably in the range of ±35° ±5°. On account of the small angle of rotation, the tendency of the brush to thread its way into the interproximal space because of the twisted two-wire arrangement of the stem is practically reduced to zero, the more so since a minor threading action, if any, during an oscillation cycle is canceled by the succeeding cycle. Practical tests have shown that such an oscillatory drive of the brush even assists the user in inserting the brush into the interproximal space as desired.

In still another feature of the present invention, the stem of the brush is arranged substantially normal to a common longitudinal axis of the handle member and the brush member. This angled position of the brush relative to the longitudinal axis results in an extremely simple manipulation of the toothbrush, making it easy for the user to guide the brush parallel to the tooth outer or inner surfaces as well as vertically thereto. It will be understood that the brush of the present invention may find advantageous application in manually as well as electrically operated toothbrushes.

Figure 2A:
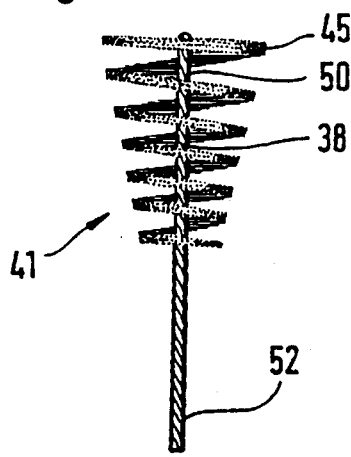
Figure 3A:
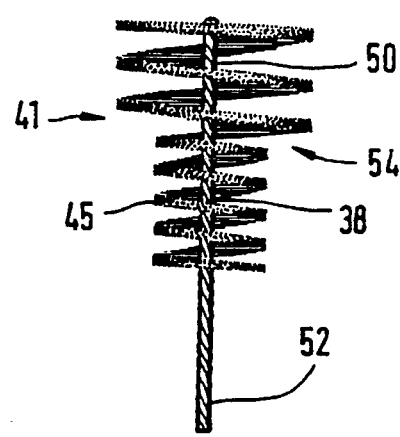
Figure 2B:
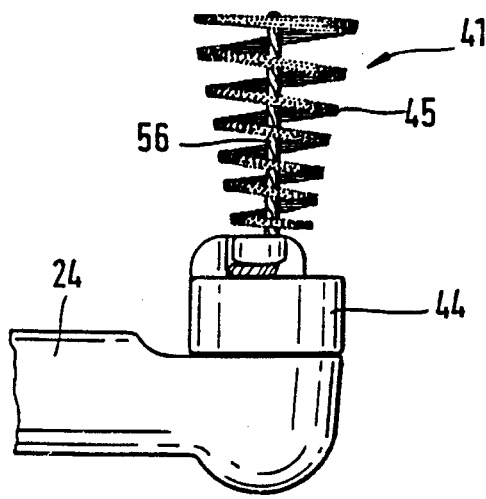
Figure 3B:
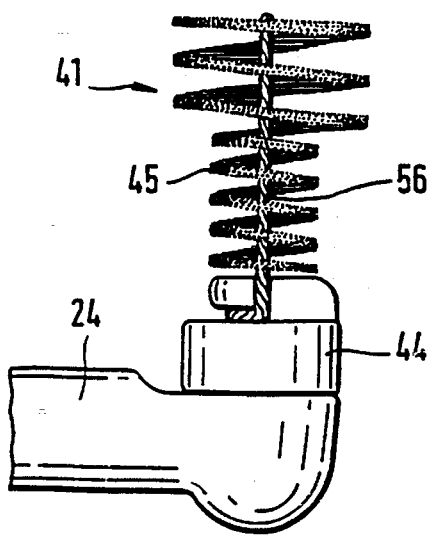
Figure 4A:
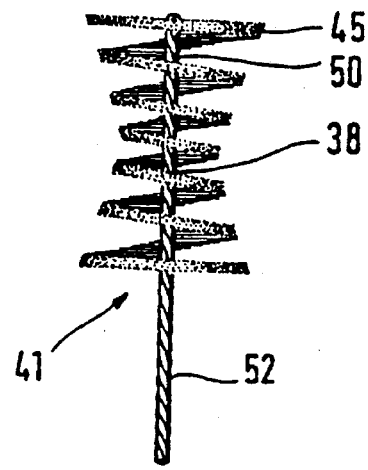
Figure 4B:
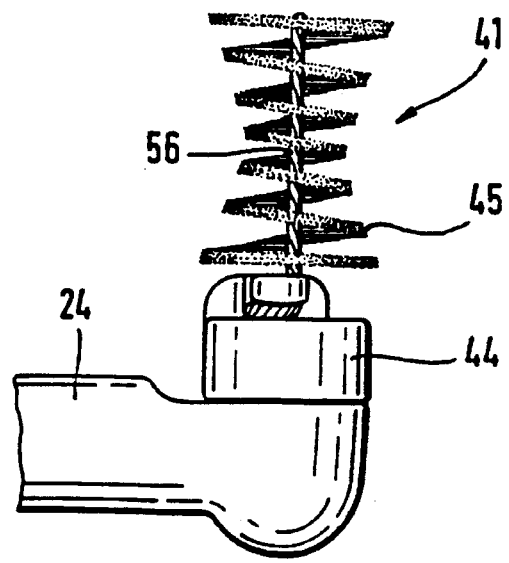
Figure 7C:
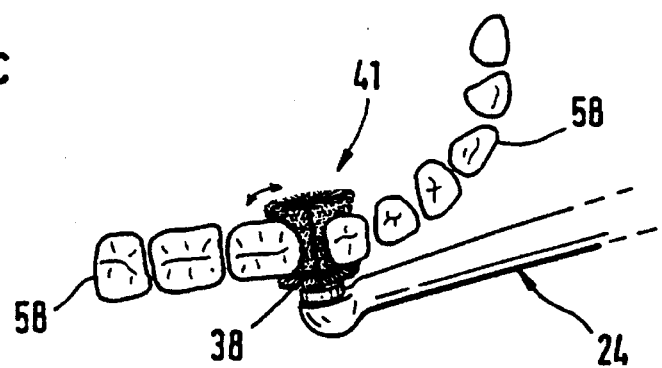
Figure 5:
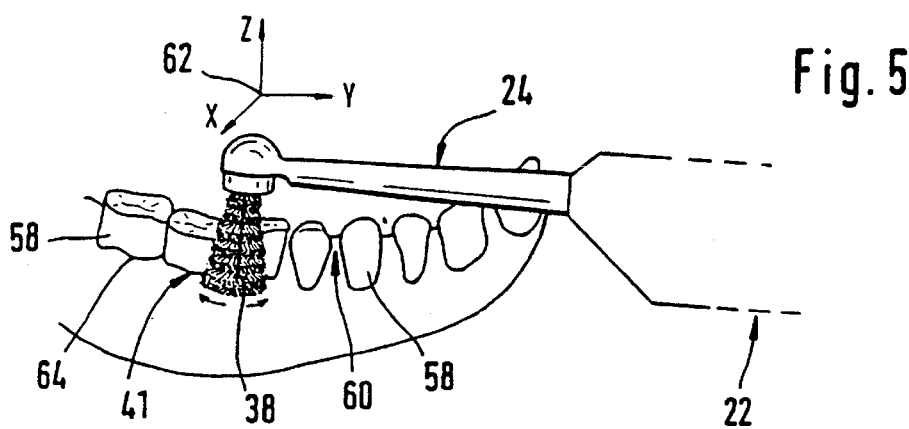
Figure 6:
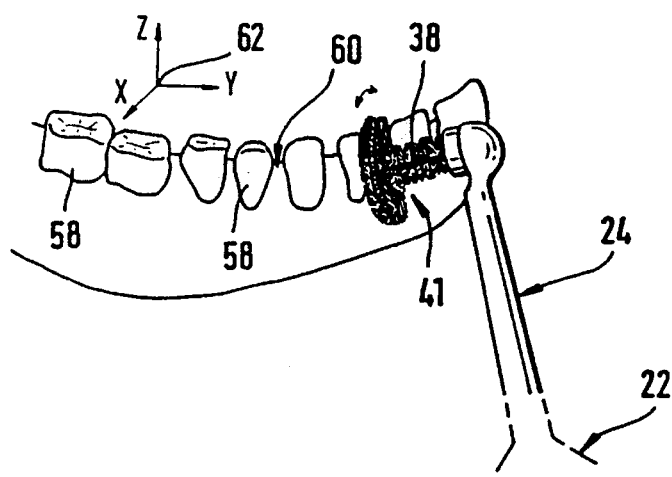
Figure 7A:
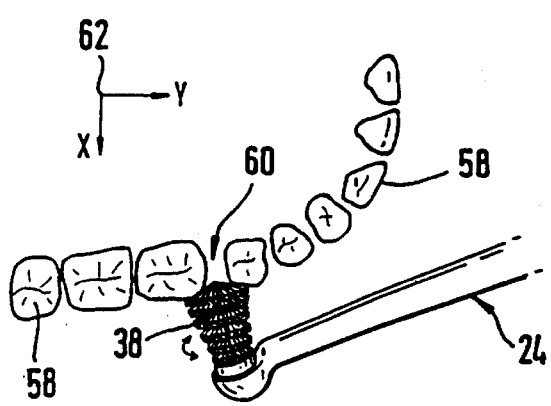
Figure 7B:
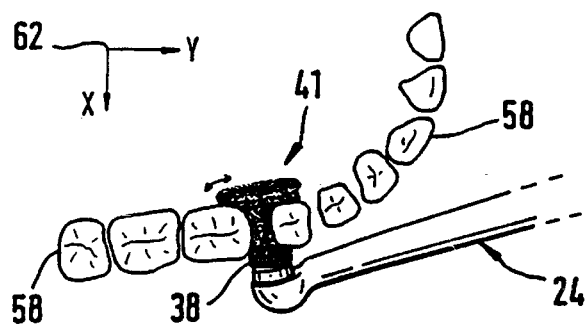

Further features, advantages and application possibilities of the present invention will become apparent from the subsequent description of embodiments illustrated in more detail in the accompanying drawings. It will be understood that all features described and/or represented by illustration, whether taken alone or in any desired combination, constitute the subject-matter of the present invention, irrespective of their summarization in the claims and their back-references. In the drawings, FIG. 1 is a schematic side view of an electric toothbrush;

FIGS. 2 a, b are views of a first embodiment of a brush showing it in a position detached from and, respectively, attached to, the brush holder;

FIGS. 3 a, b are views of a second embodiment of a brush showing it in a position detached from and, respectively, attached to, the brush holder;

FIGS. 4 a, b are views of a third embodiment of a brush showing it in a position detached from and, respectively, attached to, the brush holder; and FIGS. 5, 6, 7 a, b, c are, respectively, views of various brush positions relative to the teeth to explain the possible cleaning movements.

In the Figures, reference numeral 20 identifies an electric toothbrush. The toothbrush 20 is comprised of a handle member 22 and a brush member 24 adapted to be coupled thereto. The handle member 22 accommodates an accumulator 26 or, alternatively, a battery. The handle member further receives therein an electric motor 28 and a converter arrangement 30 for converting the continuous rotary motion of the electric motor into a rotary motion reversing direction in alternating sequence. A switch 32 for activation of the toothbrush 20 is provided on the outside of the handle member 22. The brush member 24 includes a hollow mounting tube 36 receiving a shaft 34. The mounting tube 36 and the shaft 34 are adapted to be connected with the handle member 22 by a coupling means 40 not shown in greater detail. At the end of the brush member 24 remote from the handle member 22, a brush 41 fixedly secured to a brush holder 44 is provided. The brush 41 includes a rod-shaped stem 38 serving as a bristle supporting structure from which circumferentially distributed bristles 45 extend in a radial direction. It will be understood that this circumferential distribution need not be a uniform distribution. The bristles may, of course, also be locally concentrated on the circumference so that the bristles are more or less thickly set in alternating sequence. Through a bevel gearing 42, the shaft 34 causes the brush holder 44 to perform a rotary motion reversing direction in alternating sequence. To accomplish this, a bevel gear 46 arranged at the base of the brush holder 44 cooperates with a bevel gear segment 48 provided at the head end of the shaft 34.

The axis of rotation of the brush holder 44 or the brush 41 defines a substantially right angle with respect to the axis of rotation of the shaft 34 or a common longitudinal axis of the handle member 22 and the brush member 24. However, this angle may also depart from the right angle by an amount of ±60° without limiting the present invention. The range of the angle of rotation covered by the brush holder 44 or the brush 41 may assume values in the range of between ±20° and ±100°. A value in the range of about ±35° ±5° is, however, preferred. The toothbrush of FIG. 1 is described in detail in applicant's International Patent Application Publication No. WO 91/07116 (Code No. 05537) whose contents are included in the disclosure content of the present application by express reference.

The brush 41 is comprised of an in particular rod-shaped stem 38 which may be formed, for example, by a twisted two-wire arrangement 56 (FIGS. 2 *b*, 3 *b*, 4 *b*). Prior to twisting the two-wire arrangement 56, the bristles 45 are inserted into the space intermediate the wires of the two-wire arrangement 56. For fixedly securing the bristles 45 to the bristle supporting structure configured as stem 38, the two-wire arrangement 56 is subsequently twisted such as to obtain a spiral arrangement of the individual bristles 45 with respect to the stem 38. The bristles 45 are preferably radially arranged relative to the stem 38, extending in a circumferentially distributed, preferably uniform pattern. The stem 38 may also be configured as an integrally formed plastic member in which the bristles 45 are fixedly held by injection molding the plastic material around them or by similar known fastening techniques.

The stem 38 has a first end portion 50 and a second end portion 52. Starting from the first end portion 50, the stem 38 is set with bristles 45 over a major area, while the area of the second end portion 52 of the stem has no bristles fixedly secured thereto. The section of the stem 38 carrying no bristles in the area of the second end portion 52 serves to locate the brush 41 in position on the brush holder 44. This location may be accomplished, for example, by injection molding plastic material around the portion of the stem 38 carrying no bristles, by clamping or similar fastening means. Starting from the first end portion 50, the stem 38 is equipped with bristles 45 of a predetermined length, with the length of the bristles decreasing in the direction of the second end portion 52 of the stem 38.

According to the embodiment of FIG. 2, the length of the bristles decreases linearly in the direction of the second end portion 52, causing the brush 41 to be in the form of a circular cone or frustum of a cone, with the largest radius of the circular cone being provided in the area of the first end portion 50. The maximum diameter of the brush 41 preferably assumes values in the range of 10±2 mm, this diameter diminishing for a frustoconical brush 41 to minimum diameters in the range of 5±2 mm.

In the area of the first end portion 50, bristles 45 of a thickness greater than in the remaining area of the brush 41 are preferably provided. Thus it has proven to be advantageous to provide the bristles with a thickness in the range of 6±1 mils in the area of the largest diameter of the brush 41 (1 mil corresponding to 0.0254 mm). The balance of the brush 41 is formed by bristles 45 of a thickness in the range of 4±1 mils.

In a further embodiment of the brush 41 (FIG. 3), the length of the bristles 45 diminishes in steps with the distance to the first end portion 50 of the stem 38 increasing. This embodiment provides a single step 54 arranged at a level of about one third of the overall length of the bristled portion of the brush 41, starting from the first end portion 50. The shape of this brush 41 resembles two cylinders arranged in tandem, whereof the first cylinder has a diameter larger than the second cylinder. Preferably, the larger cylinder has a diameter in the range of 12±2 mm, while the smaller cylinder has a diameter in the range of 6±2 mm. Advantageously, the bristles of the larger cylinder have a thickness in the range of 6±1 mils, and the bristles of the smaller cylinder have a thickness in the range of 4±1 mils.

In the embodiment of FIG. 4, starting from the first end portion 50, the length of the bristles 45 initially diminishes in the direction of the center of the bristled portion of the stem 38, subsequently increasing again in the direction of the second end portion 52. As a result, the brush 41 has the shape of two frustums of a cone having their smaller-diameter surface areas adjacent to each other, so that the diameter of the brush 41 is at a minimum approximately in the center and at a maximum at the respective ends of the bristled portion. The length of the area in which the length of the bristles 45 decreases towards the center substantially corresponds to the length of the area in which the length of the bristles 45 increases again starting from the center. The smallest diameter of the brush 41 thus lies essentially symmetrically in the center of the bristled portion of the stem 38. The decrease and increase in the length of the bristles 45 towards the center and, respectively, away from the center preferably occurs in linear fashion.

The largest diameter of the brush 41 in the direction of the first and the second end portion 50 and, respectively, 52 preferably assumes values in the range of 8±2 mm, whereas the smallest diameter of the brush 41 preferably amounts to values in the range of 4±2 mm. The bristle thickness preferably amounts to values in the range of 6±1 mils (1 mil corresponding to 0.0254 mm).

While FIGS. 2 *a*, 3 *a*, 4 *a* show a brush 41 in detached condition, FIGS. 2 *b*, 3 *b*, 4 *b* illustrate the brush 41 fixedly secured to the brush holder 44. It will be seen that the stem 38 which is configured in particular as a two-wire arrangement 56 defines an approximately right angle with a centerline of the brush member 24. The drive motor of the toothbrush 20 causes the brush 41 to perform an oscillating rotary motion about the axis of the bristle supporting structure, with the angle of rotation which reverses direction in alternating sequence assuming values in the range of preferably ±35°.

The possible positions of the brush 41 relative to the teeth 58 for cleaning especially the interproximal spaces 60 or gingival-tooth boundaries 64 are explained in more detail with reference to FIGS. 5, 6 and 7. To clean the gingival-tooth boundaries 64 or the entry areas of the interproximal spaces 60, the stem 38 of the brush 41 which may be of a conical, double-conical or stepped configuration is guided in the Z-Y plane of the system of coordinates 62, in particular in the direction Z, along the tooth outer or inner surfaces.

The system of coordinates 62 shall be interpreted as a system related to a single tooth, the outer or inner surfaces of each tooth 58 thus lying in the Z-Y plane and the interproximal spaces 60 in the Z-X plane. In the use of the stepped brush 41, particular effective cleaning of the interproximal spaces 60 may be accomplished when the stem 38 is substantially guided along the direction Y of the system of coordinates 62. When manipulated in this manner, the stepped brush 41 has the advantage of enabling the larger-diameter cylinder to enter into the interproximal spaces 60, the smaller-diameter cylinder then bearing against the tooth outer or inner surface.

When the brush 41 is moved into an interproximal space 60 in the direction of the X-axis (FIGS. 7 *a, b, c*), the longer-length bristles on the first end portion 50 of the stem 38 protect both the teeth 58 and the gums against contact with the stem 38 (FIG. 7 *a*). Where, for example, illness or natural growth has caused the interproximal spaces to be so large that the brush 41 fits entirely into the interproximal space 60 (FIG. 7 *b*), the teeth 58 as well as the gums are equally protected against contact with the stem 38 by the bristles arranged in the center portion of the brush 41.

In the use of the double-conical brush 41 (FIG. 4), cleaning of interproximal spaces 60 can be performed particularly effectively because the larger diameter at the respective ends automatically holds the brush 41 within the interproximal space 60 (FIG. 7 *c*). Unintentional disengagement of the brush 41 from the interproximal space 60 is prevented from occurring. This facilitates cleaning of the interproximal space 60 substantially.

The oscillatory drive of the brush 41 ensures an effective cleaning function of the brushes 41, the special configuration of the brushes 41 avoiding damage to the teeth or injury of the gums to the largest possible degree.

Further, the oscillating motion of the brush within an angular range of about ±35° ±5° ensures that in the use of a stem 38 comprised of a twisted two-wire arrangement 56, the brush is prevented from threading itself into an interproximal space 60 as could happen in cases where a rotary drive of the brushes 41 is employed.

This substantial advantage, that is, the elimination of the possibility of a brush threading itself into an interproximal space by providing for an oscillatory motion of the brush, is fully independent of the shape of the brush and, accordingly, may also be achieved with prior known brushes.

The arrangement of the stem 38 of the brush 41 essentially normal to a longitudinal axis of the brush member 24 or the handle member 22 allows the user to manipulate the brush 41 in a wide variety of hand-adapted positions relative to the teeth 58 or interproximal spaces 60 to be cleaned.

We claim:

1. A toothbrush system for cleaning interproximal spaces between a user's teeth, comprising a handle member, a brush member coupled to said handle member, said brush member comprising a brush holder, a bristle supporting structure, and an array of bristles, said bristle supporting structure comprising a rod-shaped stem having first and second end portions, said stem comprising a twisted two-wire arrangement, said stem carrying no bristles in the region of said second end portion, said bristles being fixedly secured between the wires of said two-wire arrangement in said first end portion so that said array of bristles extend radially relative to said stem in the region of said first end portion and are arranged in a circumferentially distributed pattern, said stem extending away from said brush holder thereby allowing the first end portion of said stem along with said array of bristles to be inserted into the interproximal spaces between the user's teeth during use, said system further comprising a motor drive mechanism in said handle member for driving said bristle array in oscillating rotary motion about the axis of said stem, wherein the lengths of said bristles are larger at a distal end of said first end portion of said stem than in a region in the center of the bristled portion of said stem, said distal end of said first portion being the end of said first portion that is remote from said second portion.

2. The system of claim 1 wherein said stem of said brush is arranged substantially normal to a longitudinal axis of said brush member.

3. The system of claim 1 wherein starting from the distal end of said first end portion of said stem, the lengths of said bristles diminish initially in the direction of the center of said bristle array and subsequently increase again in the portion of said bristle array more proximate to said second end portion.

4. The system of claim 3 wherein the lengths of the bristles in said bristle array initially decrease linearly with the axial distance from the distal end of said first end portion of said stem and subsequently increase again linearly.

5. The system of claim 3 wherein the smallest diameter of said brush is provided symmetrically in the center of said bristle array.

6. The system of claim 3 wherein the diameter of said bristle array decreases initially from a value in the range of 8±2 millimeters to a value in the range of 4±2 millimeters, subsequently increases again to a value in the range of 8±2 millimeters.

7. The system of claim 3 wherein bristles in said array have a thickness in the range of 6±1 mils (1 mil corresponding to 0.0254 millimeters).

8. The system of claim 1 wherein the axial length of said bristle array is in the range of 12±3 millimeters, and the length of the portion of said stem carrying no bristles is in the range of 9±3 millimeters.

9. The system of claim 1 wherein said handle member has a longitudinal axis and wherein said stem of the brush member is arranged substantially normal to the longitudinal axis of said handle member.

10. The system of claim 9 wherein the length of said bristles is larger in the region of said first end portion of said stem than in a region in the center of the bristled portion of said stem.

11. The system of claim 9 wherein the diameter of said bristle array decreases initially from a value in the range of 8±2 millimeters to a value in the range of 4±2 millimeters, subsequently increases again to a value in the range of 8±2 millimeters.

12. The system of claim 11 wherein said two-wire arrangement providing a spiral arrangement of individual bristles in said array.

13. The system of claim 12 wherein the axial length of said bristle array is in the range of 12±3 millimeters, and the length of the portion of said stem carrying no bristles is in the range of 9±3 millimeters.

14. The system of claim 1 wherein said motor drive mechanism drives said bristle array at an angle of oscillation in the range of ±20° to ±100°.

15. A toothbrush system for cleaning interproximal spaces between a user's teeth, comprising a handle member, a brush member coupled to said handle member, said brush member comprising a brush holder, a bristle supporting structure, and an array of bristles, said bristle supporting structure comprising a rod-shaped stem having first and second end portions, said stem carrying no bristles in the region of said second end portion, said array of bristles extending radially relative to said stem in the region of said first end portion and being arranged in a circumferentially distributed pattern, the lengths of said bristles diminishing initially from a distal end of said first end portion of said stem toward the center of said bristle array and subsequently increasing again in the portion of said bristle array more remote from the distal end of said first end portion, the distal end of said first end portion being the end of said first portion that is most remote from the second portion, said stem extending away from said brush holder thereby allowing the first end portion of said stem along with said array of bristles to be inserted into the interproximal spaces between the user's teeth during use, said system further comprising a motor drive mechanism in said handle member for driving said bristle array in oscillating rotary motion about the axis of said stem.

16. The system of claim 15 wherein the length of bristles in said bristle array initially decreases linearly with the axial distance from the distal end of said first end portion of said stem and subsequently increases again linearly.

17. The system of claim 15 wherein the smallest diameter of said brush is provided symmetrically in the center of said bristle array.

18. The system of claim 15 wherein the diameter of said bristle array decreases initially from a value in the range of 8±2 millimeters to a value in the range of 4±2 millimeters, subsequently increases again to a value in the range of 8±2 millimeters.

19. The system of claim 15 wherein bristles in said array have a thickness in the range of 6±1 mils (1 mil corresponding to 0.0254 millimeters).

20. The system of claim 15 wherein said stem comprises a twisted two-wire arrangement, and said bristles are fixedly secured between the wires of said two-wire arrangement.

21. The system of claim 15 wherein said motor drive mechanism drives said bristle array at an angle of oscillation in the range of ±20° to ±100°.

\* \* \* \* \*